United States Patent
Zhang et al.

(10) Patent No.: US 10,376,288 B2
(45) Date of Patent: Aug. 13, 2019

(54) FIXING AND CONNECTING APPARATUS WITH STRESS-DISPERSING CAPABILITY FOR ANTERIOR SUPERIOR SPINE AND ILIAC CREST

(71) Applicant: Yingze Zhang, Shijiazhuang, Hebei Province (CN)

(72) Inventors: Yingze Zhang, Shijiazhuang (CN); Wei Chen, Shijiazhuang (CN); Juan Wang, Shijiazhuang (CN); Qi Zhang, Shijiazhuang (CN)

(73) Assignee: Yingze Zhang, Shijiazhuang, Hebei (CN)

( * ) Notice: Subject to any disclaimer, the term of this patent is extended or adjusted under 35 U.S.C. 154(b) by 838 days.

(21) Appl. No.: 14/896,720

(22) PCT Filed: Feb. 25, 2015

(86) PCT No.: PCT/CN2015/073267
§ 371 (c)(1),
(2) Date: Dec. 8, 2015

(87) PCT Pub. No.: WO2015/139549
PCT Pub. Date: Sep. 24, 2015

(65) Prior Publication Data
US 2016/0128730 A1    May 12, 2016

(30) Foreign Application Priority Data
Mar. 19, 2014   (CN) .......................... 2014 1 0102114

(51) Int. Cl.
*A61F 2/46*   (2006.01)
*A61B 17/68*   (2006.01)
*A61B 17/88*   (2006.01)

(52) U.S. Cl.
CPC .......... *A61B 17/68* (2013.01); *A61B 17/8869* (2013.01); *A61B 2017/681* (2013.01)

(58) Field of Classification Search
None
See application file for complete search history.

(56) References Cited

U.S. PATENT DOCUMENTS

| 4,185,623 A | 1/1980 | Volkov et al. |
| 4,938,762 A | 7/1990 | Wehrli |

(Continued)

FOREIGN PATENT DOCUMENTS

| CN | 2265765 Y | 10/1997 |
| CN | 101011300 A | 8/2007 |

(Continued)

OTHER PUBLICATIONS

International Search Report for International Application No. PCT/CN2015/073267, dated May 21, 2015, with English translation.
The 1st OA issued by CNIPA dated Jul. 9, 2014.

*Primary Examiner* — Sameh R Boles
(74) *Attorney, Agent, or Firm* — Yunling Ren (57) ABSTRACT

Disclosed is a fixing and connecting apparatus with stress-dispersing capability for anterior superior spine and iliac crest, comprising: two side splints disposed opposite, which connects with each other at upper ends, with the shape of upper end at the inner wall of the two side splints coinciding with the shape of the upper surface of the anterior superior spine and iliac crest, and a cavity defined by the inner walls of the two side splints matching with the profile of the anterior superior spine and iliac crest; a fixing hole which is provided inclined downwards at upper part of at least one of the side splints with a diameter matching with the diameter of a kirschner pin; and a connecting structure which is (Continued)

provided at the upper part of any one of the side splints for connecting to a traction apparatus.

13 Claims, 5 Drawing Sheets

(56) References Cited

U.S. PATENT DOCUMENTS

| | | | | |
|---|---|---|---|---|
| 5,697,933 | A | * 12/1997 | Gundlapalli | ....... A61B 17/1714 606/206 |
| 2005/0107787 | A1 | 5/2005 | Kutsenko | |

FOREIGN PATENT DOCUMENTS

| | | |
|---|---|---|
| CN | 102014774 A | 4/2011 |
| CN | 103263289 A | 8/2013 |
| CN | 203183015 U | 9/2013 |
| CN | 203749534 U | 8/2014 |
| RU | 2180533 C2 | 3/2002 |

* cited by examiner

FIXING AND CONNECTING APPARATUS WITH STRESS-DISPERSING CAPABILITY FOR ANTERIOR SUPERIOR SPINE AND ILIAC CREST

CROSS REFERENCE TO RELATED APPLICATIONS

This application is an US national phase of International Application No. PCT/CN2015/073267, filed on Feb. 25, 2015, which is based upon and claims priority to Chinese Patent Application No. 201410102114.7 filed on Mar. 19, 2014, and the entire contents thereof are incorporated herein by reference.

TECHNICAL FIELD

The present disclosure relates to a field of medical apparatus for orthopedic operation, particularly, relates to a fixing and connecting apparatus used for traction treatment to anterior superior spine and iliac crest.

BACKGROUND

Femoral shaft fracture and the distal femur fracture are common fracture clinically. Operation is a preferred treatment which includes fixing with intramedullary nail and reconstruction plate. Since leg muscle quadriceps such as femoris muscle has strong power, muscle will be shortening deformity by traction if femur is fractured, which results in difficulty in reduction, length restoration and maintain with effect. If anatomical reduction is not performed during operation, complication such as malunion and pool limb alignment will be occurred after operation. Therefore, traction during operation is an important treatment for reduction of femoral fracture and length restoration of lower limbs.

Currently, the basic method of traction operation by structure of artificial auxiliary or traction apparatus, is that: on one hand, fixing a fixed end of the bone of the patient, on the other hand, drawing outwards fracture portion away from the fixed end so as to recover the full length of the lower limbs. With the development of technology, traction apparatus are widely used in clinical femoral fracture traction. During traction using traction and reduction apparatus, it is required to drill a steinmann pin (or kirschner pin) into the anterior superior spine or other part at the iliac crest of the patient to act as a pivot for connecting the traction and reduction apparatus. However, for patients with osteoporosis or requiring large traction force, the steinmann pin would break the iliac crest or bone, which results in the traction failure and brings out difficulties to future treatment. Therefore, it is a problem required to be solved quickly that how to avoid the damage to the anterior superior spine and iliac crest, and apply enough traction force to the femoral fracture portion during traction.

The foresaid information as disclosed in the background part only serves to enhance understanding of the background of the disclosure, thereby it may not contain ordinary skill information that has been well known.

SUMMARY

The technical problem to be solved by the present disclosure is to provide a fixing and connecting apparatus with stress-dispersing capability for anterior superior spine and iliac crest, which is capable of applying enough traction force to the femoral fracture portion during traction without damaging the anterior superior spine and iliac crest.

Additional aspects and advantages of the disclosure will be in part set forth in the description below, and in part will become obvious from the description, or may be learned from practice of the present disclosure.

In order to achieve the above objective, the following technical solution is adopted by the present disclosure:

In one aspect, the present disclosure provides a fixing and connecting apparatus with stress-dispersing capability for anterior superior spine and iliac crest, wherein it comprises: two side splints, which are disposed opposite to each other and connected with each other at upper ends thereof, the shape of the upper end at the inner wall of the two side splints coincides with the shape of an upper surface of the anterior superior spine and iliac crest, and a cavity defined by the inner walls of the two side splints matches with the profile of the anterior superior spine and iliac crest; a fixing hole is provided inclined downwards at upper part of at least one of the side splints with a diameter matching with the diameter of a kirschner pin; and a connecting structure is provided at the upper part of any one of the side splints for connecting to a traction apparatus.

In an embodiment of the present disclosure, wherein two flat plates extend upwards from the upper part of the two side splints respectively with a rotating shaft connecting the lower ends of the two flat plates; and a supporting spring is provided between inner faces of the two flat plates above the rotating shaft.

In an embodiment of the present disclosure, wherein a threaded rod is provided between the flat plates with nuts screwed at both ends of the threaded rod, the nuts disposed at outside of the two flat plates, and the supporting spring is sleeved around the threaded rod.

In an embodiment of the present disclosure, wherein lower ends of the two side splints bend inwards and provided with a line of zigzag at an edge of the lower end.

In an embodiment of the present disclosure, wherein the connecting structure provided at the upper part of the side splint for connecting to a traction apparatus is a connecting seat having a circle hole at center with the diameter matching with the diameter of a steinmann pin.

In an embodiment of the present disclosure, wherein a fixing hole is disposed at each side splint, two fixing holes at two side splint are opposite each other.

In an embodiment of the present disclosure, wherein the two side splints are connected integrally at the upper ends by a top plate, a front splint and a rear splint are connected to the front end and the rear end of the top plate respectively, the front splint and the rear splint are bend to form an arch at the front ends, and provide with a line of zigzag at a lower edges, and a connecting structure is provided at the top surface of the top plate for connecting to the traction apparatus.

In an embodiment of the present disclosure, wherein fixing holes are disposed at the front splint and rear splint respectively with a diameter matching with the diameter of the kirschner pin.

In an embodiment of the present disclosure, wherein the connecting structure provided at the top surface of the top plate for connecting to the traction apparatus is a connecting seat having a circle hole at center with the diameter matching with the diameter of the steinmann pin.

In an embodiment of the present disclosure, wherein the connecting structure provided at the top surface of the top plate for connecting to the traction apparatus is a connecting rod having a lower end connecting to the top surface of the top plate and an upper end being a spherical part; the spherical part at the upper end of the connecting rod matches with a ball-and-socket structure at the front end of a reduction rod in a traction device for femoral fracture.

According to the above technical solutions, the present disclosure has following advantageous technical effects:

Firstly, the fixing and connecting apparatus stress-dispersing capability for anterior superior spine and iliac crest according to the present disclosure includes two side splints matching with the profile of the anterior superior spine and iliac crest. During operation, two side splints tightly clip the upper end of the anterior superior spine and iliac crest, and the force of the reduction rod of the traction device is exerted onto the fixing and connecting apparatus. The cavity defined by the inner walls of the side splints of the fixing and connecting apparatus matches with the profile of the anterior superior spine and iliac crest, therefore, the side splints contact with the anterior superior spine and iliac crest, which could increase the force bearing area of the anterior superior spine and iliac crest, thus dispersing force. Consequently, the anterior superior spine and iliac crest could bear large traction force without being damaged under stress.

Further, a zigzag provided at the edge at the lower end of two side splints could play a role in fixing assistantly.

Moreover, the Kirschner pins can be inserted into the opposite fixing holes, which are set on the side splints, the front splint and rear splint respectively, to assist the fixation.

The present disclosure has the advantages of simple structure, convenient use, and good effect, which effectively disperses stress suffered by the anterior superior spine and iliac crest during traction and fixing, enable the traction apparatus to apply enough traction force to the femoral fracture portion without damaging the anterior superior spine and iliac crest during traction. Therefore, the present disclosure could solve the problem unsolved for a long time that the anterior superior spine and iliac crest may be damaged during traction.

The above and other features and advantages of the present disclosure will become more apparent from the detailed description of exemplary embodiments thereof with reference to accompany drawings.

Reference numerals in the above drawings are as follows: side splint 1, flat plate 2, rotation shaft 3, supporting spring 4, fixing hole 5, zigzag 6, top plate 7, front splint 8, rear splint 9, connecting seat 10, connecting rod 11, kirschner pin 12, steinmann pin 13, threaded rod 14, and nut 15.

DETAILED DESCRIPTION

Specific embodiments in this disclosure have been shown by examples in the foregoing drawings and are hereinafter described in detail. The figures and written description are not intended to limit the scope of the inventive concepts in any manner. Rather, they are provided to illustrate the inventive concepts to a person skilled in the art by reference to particular embodiments. The same or similar features employ identical reference numerals, and the detailed description thereof is omitted.

Main structures of the present disclosure include two side splints 1 disposed opposite each other, which connects with each other at upper ends. The shape of upper end at the inner wall of the two side splints 1 coincides with the shape of the upper surface of the anterior superior spine and iliac crest, and a cavity defined by the inner walls of the two side splints 1 matches with the profile of the anterior superior spine and iliac crest. The two side splints 1 could clip at the edge of the anterior superior spine and iliac crest with the faces thereof tightly closes to both sides of the anterior superior spine and iliac crest. A fixing hole 5 is provided inclined downwards at upper part of any one of the side splints 1 with a diameter matching with the diameter of the kirschner pin 12. After the side splints 1 clipping, the side splints 1 and the anterior superior spine and iliac crest are fixed together by the kirschner pin 12 through the fixing hole 5. A connecting structure is provided at the upper part of any one of the side splints 1 for connecting to a traction apparatus.

The various structures, which are derived the main structures described above, are disclosed herein.

Figure 1:
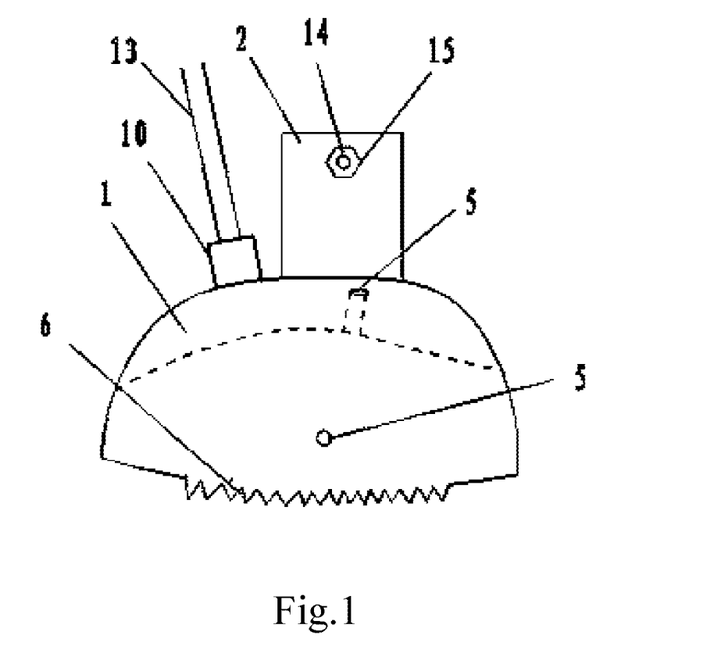
FIG. 1 is a schematic view according to an embodiment of the present fixing and connecting apparatus with stress-dispersing capability for anterior superior spine and iliac crest.
Figure 2:
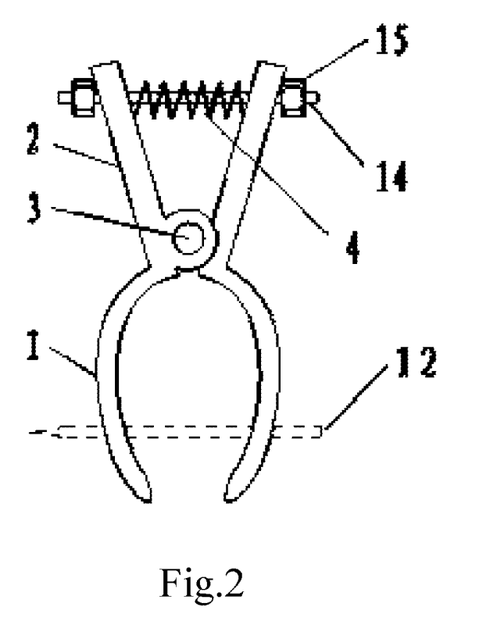
FIG. 2 is a side view of FIG. 1.

As shown in FIGS. 1 and 2, according to one embodiment of present fixing and connecting apparatus with stress-dispersing capability for anterior superior spine and iliac crest includes two side splints 1, and flat plates 2 extending upwards from the upper part of the two side splints 1 respectively with a rotating shaft 3 connecting the lower ends of the extending flat plates 2. A threaded rod 14 is provided between the two flat plates 2 above the rotating shaft 3 with nuts 15 screwed at both ends of the threaded rod 14. The nuts 15 disposed at outside of the two flat plates 2. A supporting spring 4 is sleeved around the threaded rod 14 and between inner faces of the two flat plates 2. Therefore, a clip is formed by the two side splints 1. The two side splints may clip at the edge of the anterior superior spine and iliac crest by elastic force of the supporting spring 4, and the traction force of the traction apparatus could exert onto the anterior superior spine and iliac crest through the side splints 1, which could increase the force bearing area of the anterior superior spine and iliac crest and disperse force. Consequently, the anterior superior spine and iliac crest could bear large traction force without being damaged under stress.

As shown in FIG. 1, the lower ends of the two side splints 1 bend inwards and provided with a line of zigzag 6 at the edge of the lower ends respectively. The zigzag 6 could pierce into the bone cortex so as to play a role of fixing assistantly.

As shown in FIG. 1, a connecting structure is provided at the upper part of the side splints 1 for connecting to the traction apparatus. A connecting seat 10 may be used as the above connecting structure, which has a circle hole at center with the diameter matching with the diameter of the steinmann pin 13. The steinmann pin 13 may be directly inerted into the circle hole of the connecting seat 10 so as to exert force to the side splints 1.

As shown in FIG. 1, fixing holes 5 are provided at the two side splints 1 respectively with the diameter matching with the diameter of the kirschner pin 12. The kirschner pin 12 pierces into the bone cortex from outside to inside so as to firmly fix the fixing and connecting apparatus.

Figure 3:
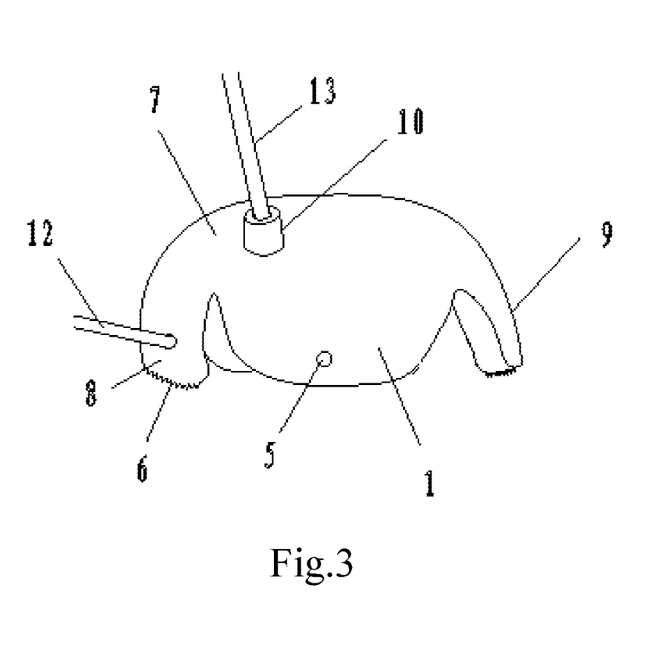
FIG. 3 is a schematic view according to another embodiment of the present fixing and connecting apparatus with stress-dispersing capability for anterior superior spine and iliac crest.
Figure 4:
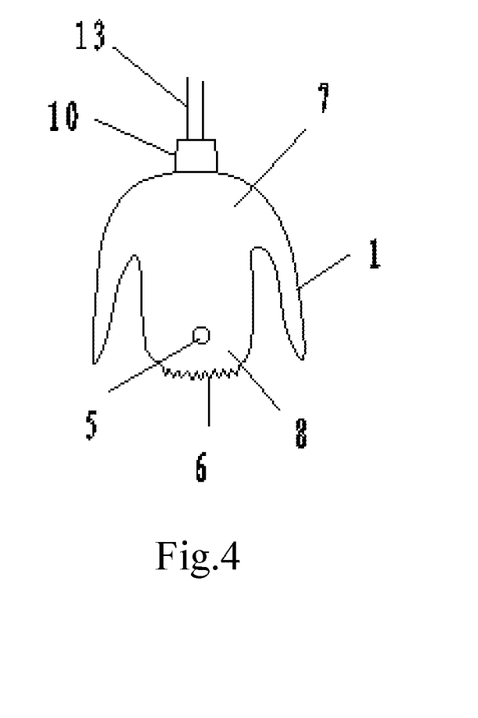
FIG. 4 is a side view of FIG. 3.

As shown in FIGS. 3 and 4, according to another embodiment of the and fixing and connecting apparatus with stress-dispersing capability for anterior superior spine and iliac crest, it includes two side splints 1 which are connected integrally at the upper ends by a top plate 7. A front splint 8 and a rear splint 9 are connected to the front end and the rear end of the top plate 7 respectively. The front splint 8 and the rear splint 9 are bend to form an arch at the front ends, and provided with a line of zigzag 6 at the lower edges respectively. During operation, the two side splints 1, front splint 8 and rear splint 9 are directly inserted into the edge of the anterior superior spine and iliac crest and tightly clipped together by elastic force of the above splints. A cavity defined by the front splint 8, rear splint 9 and two side splints 1 has a profile matching the anterior superior spine and iliac crest, therefore, after clipping at the front end, rear end and both sides of the anterior superior spine and iliac crest, the fixing and connecting apparatus could tightly clip the anterior superior spine and iliac crest without disassembly or shaking, and the force will be stably dispersed.

As shown in FIGS. 3 and 4, a fixing hole 5 is disposed at each side splint 1, two fixing holes 5 at two side splint 1 are opposite to each other. Fixing holes 5 are disposed at the front splint 8 and rear splint 9 respectively with a diameter matching with the diameter of the kirschner pin 12. The kirschner pin 12 pierces into the front or rear part of the anterior superior spine and iliac crest through the fixing holes 5 of the front splint 8 or rear splint 9, and inserts into the cortex at both sides of the ilium from outside to inside, such that the fixing and connecting apparatus and the anterior superior spine and iliac crest could be firmly connected.

As shown in FIGS. 3 and 4, in an embodiment, a connecting structure is provided at the top surface of the top plate 7 for connecting to a traction apparatus. A connecting seat 10 may be used as the above connecting structure, which has a circle hole at center with the diameter matching with the diameter of the steinmann pin 13.

Figure 5:
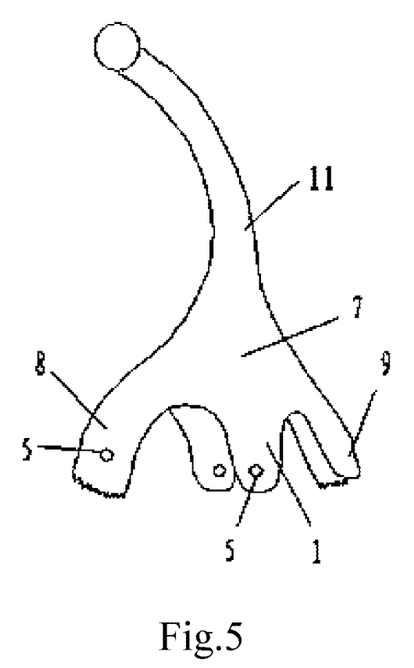
FIG. 5 is a schematic view according to further embodiment of the present fixing and connecting apparatus with stress-dispersing capability for anterior superior spine and iliac crest.

As shown in FIG. 5, in an embodiment, a connecting structure is provided at the top surface of the top plate 7 for connecting to a traction apparatus. A connecting rod 11 may be used as the above connecting structure, which has a lower end connecting to the top surface of the top plate 7 and an upper sphere-shaped end. The spherical part at the upper end of the connecting rod 11 matches with a ball-and-socket structure at the front end of a reduction rod of a traction device for femoral fracture so as to connect to the ball-and-socket structure.

The fixing and connecting apparatus with stress-dispersing capability for anterior superior spine and iliac crest according to the present disclosure may be operated as follows:

Placing the fixing and connecting apparatus according to the present disclosure at the upper end of the anterior superior spine and iliac crest with two side splints 1 tightly clipping both sides of the anterior superior spine and iliac crest, selectively using the kirschner pin 12, two side splints 1, front splint 8 or rear splint 9 to connect to the anterior superior spine and iliac crest depending upon the situation so as to keep a stable connecting condition. After fixing, inserting the steinmann pin 13 at the front end of the reduction rod of a traction device for femoral fracture into the circle hole of the connecting seat 10, or connecting the ball-and-socket structure at the front end of the reduction rod of a traction device for femoral fracture to the spherical part at the upper end of the connecting rod 11 of the top plate 7. After finishing the above connection, the traction device for femoral fracture may be used to perform traction for the femur. The traction force is exerted onto the anterior superior spine or iliac crest through the present disclosure, such that the force bearing area of the anterior superior spine and iliac crest is increased, thus and the force is dispersed. Consequently, the anterior superior spine and iliac crest could bear large traction force without being damaged under stress.

The concept of the present disclosure is to adopt a structure having two splints to fix the anterior superior spine and iliac crest with stress-dispersing capability. Besides to the embodiments described above, many other embodiments are feasible, therefore, the above embodiments are not intended to limit the protection scope of the present disclosure. All modifications, equivalent improvements made within the spirit and principles of the present disclosure shall fall within the protection scope of the present disclosure.

INDUSTRIAL APPLICABILITY

The fixing and connecting apparatus with stress-dispersing capability for anterior superior spine and iliac crest according to the present disclosure includes two side splints matching with the profile of the anterior superior spine and iliac crest. During operation, two side splints tightly clip the upper end of the anterior superior spine and iliac crest, and the force of the reduction rod of the traction device is exerted onto the fixing and connecting apparatus. The cavity defined by the inner walls of the side splints of the fixing and connecting apparatus matches with the profile of the anterior superior spine and iliac crest, therefore, the side splints contact with the anterior superior spine and iliac crest, which could increase the force bearing area of the anterior superior spine and iliac crest, thus dispersing force. Consequently, the anterior superior spine and iliac crest could bear large traction force without being damaged under stress.

Exemplary embodiments have been specifically shown and described as above. It is to be understood that both the foregoing general description are exemplary and explanatory only and are not restrictive of the invention. It will be appreciated the aforesaid embodiments may be modified and portions of the technical features therein may be equally changed, which does not depart from the spirit or principle. All suitable modifications and equivalent which come within the spirit and scope of the appended claims are intended to fall within the scope of the disclosure.

What is claimed is:

1. A fixing and connecting apparatus with stress-dispersing capability for anterior superior spine and iliac crest, wherein it comprises: two side splints, which are disposed opposite to each other and connected with each other at upper ends thereof, the shape of the upper end at the inner wall of the two side splints coincides with the shape of an upper surface of the anterior superior spine and iliac crest, and a cavity defined by the inner walls of the two side splints matches with the profile of the anterior superior spine and iliac crest; a fixing hole is provided inclined downwards at upper part of at least one of the side splints with a diameter matching with the diameter of a kirschner pin; and a connecting structure is provided at the upper part of any one of the side splints for connecting to a traction apparatus.

2. The fixing and connecting apparatus with stress-dispersing capability for anterior superior spine and iliac crest according to claim 1, wherein two flat plates extend upwards from the upper part of the two side splints respectively with a rotating shaft connecting the lower ends of the two flat plates;

and a supporting spring is provided between inner faces of the two flat plates above the rotating shaft.

3. The fixing and connecting apparatus with stress-dispersing capability for anterior superior spine and iliac crest according to claim 2, wherein a threaded rod is provided between the flat plates with nuts screwed at both ends of the threaded rod, the nuts disposed at outside of the two flat plates, and the supporting spring is sleeved around the threaded rod.

4. The fixing and connecting apparatus with stress-dispersing capability for anterior superior spine and iliac crest according to any one from claims 3, wherein the connecting structure provided at the upper part of the side splint for connecting to a traction apparatus is a connecting seat having a circle hole at center with the diameter matching with the diameter of a steinmann pin.

5. The fixing and connecting apparatus with stress-dispersing capability for anterior superior spine and iliac crest according to any one from claims 2, wherein the connecting structure provided at the upper part of the side splint for connecting to a traction apparatus is a connecting seat having a circle hole at center with the diameter matching with the diameter of a steinmann pin.

6. The fixing and connecting apparatus with stress-dispersing capability for anterior superior spine and iliac crest according to claim 1, wherein lower ends of the two side splints bend inwards and provided with a line of zigzag at an edge of the lower end.

7. The fixing and connecting apparatus with stress-dispersing capability for anterior superior spine and iliac crest according to any one from claims 6, wherein the connecting structure provided at the upper part of the side splint for connecting to a traction apparatus is a connecting seat having a circle hole at center with the diameter matching with the diameter of a steinmann pin.

8. The fixing and connecting apparatus with stress-dispersing capability for anterior superior spine and iliac crest according to any one from claims 1, wherein the connecting structure provided at the upper part of the side splint for connecting to a traction apparatus is a connecting seat having a circle hole at center with the diameter matching with the diameter of a steinmann pin.

9. The fixing and connecting apparatus with stress-dispersing capability for anterior superior spine and iliac crest according to claim 1, wherein a fixing hole is disposed at each side splint, two fixing holes at two side splint are opposite each other.

10. The fixing and connecting apparatus with stress-dispersing capability for anterior superior spine and iliac crest according to claim 1, wherein the two side splints are connected integrally at the upper ends by a top plate, a front splint and a rear splint are connected to the front end and the rear end of the top plate respectively, the front splint and the rear splint are bend to form an arch at the front ends, and provide with a line of zigzag at a lower edges, and a connecting structure is provided at the top surface of the top plate for connecting to the traction apparatus.

11. The fixing and connecting apparatus with stress-dispersing capability for anterior superior spine and iliac crest according to claim 10, wherein fixing holes are disposed at the front splint and rear splint respectively with a diameter matching with the diameter of the kirschner pin.

12. The fixing and connecting apparatus with stress-dispersing capability for anterior superior spine and iliac crest according to claim 10, wherein the connecting structure provided at the top surface of the top plate for connecting to the traction apparatus is a connecting seat having a circle hole at center with the diameter matching with the diameter of the steinmann pin.

13. The fixing and connecting apparatus with stress-dispersing capability for anterior superior spine and iliac crest according to claim 10, wherein the connecting structure provided at the top surface of the top plate for connecting to the traction apparatus is a connecting rod having a lower end connecting to the top surface of the top plate and an upper end being a spherical part; the spherical part at the upper end of the connecting rod matches with a ball-and-socket structure at the front end of a reduction rod in a traction device for femoral fracture.

* * * * *